United States Patent [19]

Chevion et al.

[11] Patent Number: 5,618,838

[45] Date of Patent: Apr. 8, 1997

[54] GALLIUM COMPLEXES FOR THE TREATMENT OF FREE RADICAL-INDUCED DISEASES

[75] Inventors: Mordechai Chevion; Edward Berenshtein, both of Jerusalem, Israel

[73] Assignee: Yissum Research Development Company of the Hebrew University of Jerusalem, Jerusalem, Israel

[21] Appl. No.: 569,116

[22] PCT Filed: Jun. 17, 1994

[86] PCT No.: PCT/US94/06878

§ 371 Date: Feb. 29, 1996

§ 102(e) Date: Feb. 29, 1996

[87] PCT Pub. No.: WO95/00140

PCT Pub. Date: Jan. 5, 1995

[30] Foreign Application Priority Data

Jun. 18, 1993 [IL] Israel ........................................ 106064

[51] Int. Cl.⁶ ............................... A61K 31/28; C07F 7/24
[52] U.S. Cl. ................................................ 514/492; 556/1
[58] Field of Search .................................. 514/492; 556/1

[56] References Cited

U.S. PATENT DOCUMENTS 5,328,992  7/1994  Peter et al. ................................ 534/16

Primary Examiner—Raymond Henley, III
Attorney, Agent, or Firm—Helfgott & Karas, P.C.

[57] ABSTRACT

A pharmaceutical composition comprises a gallium complex of desferrioxamine or penicillamine as active ingredients therein, in combination with a pharmacologically acceptable carrier. The gallium desferrioxamine or gallium penicillamine complex are useful in the treatment of free radical-induced pathological conditions; the treatment of injury resulting from ischemic insult to the heart, brain or kidney; the treatment of thalassemia; the treatment of hemochromatosis; the treatment of Wilson's disease; the treatment of paraquat toxicity; or for exchanging gallium for iron.

12 Claims, No Drawings

GALLIUM COMPLEXES FOR THE TREATMENT OF FREE RADICAL-INDUCED DISEASES

This application is a 371 of PCT/US 94/06878 filed Jun. 17, 1994.

The present invention relates to a pharmaceutical composition containing a gallium complex (Ga) as active ingredient therein, or a combination of Ga complex with zinc (Zn) and/or manganese (Mn) complexes, therein.

More particularly, the present invention relates to pharmaceutical preparations which are effective against iron-mediated and copper-mediated damage, said preparations being based on Gallium complexes with desferrioxamine B (desferrioxamine=DFO) or with penicillamine and preparations based on combinations of Ga, Zn and Mn complexes with DFO or with penicillamine.

Redox-active iron and copper have been demonstrated to be responsible for tissue damage in ischemia and reperfusion injury, ionizing irradiation, thaltesemia, hemochromatosis and Wilson disease. Furthermore, in a wide variety of pathologic states, the causative role of free radicals has been proposed. These metals can readily serve as effective mediators enhancing free radical-induced damage and thus have been incriminated as a major responsible species for tissue injury (M. Chevion, "A Site-Specific Mechanism for Free Radical-Induced Biological Damage: The Essential Role of Redox Active Transition Metals", *Free Radicals for Biology and Medicine,* Vol. 5, No. 1, pp. 27–37, 1988).

The present inventors have shown that the use of desferrioxamine, and better still, the combination of DFO and nitrilotriacetate (NTA) resulted in a dramatic increase in the rate of survivors in paraquat toxicity. While in control group there were no survivors, following treatment with either chelators, 25–30% survivors were monitored. The administration of a combination of these specific chelators led to 60–90% survivors (average 70%) (R. Kohen and M. Chevion, "Paraquat Toxicity Is Enhanced by Iron and Inhibited by DFO in Laboratory Mice", *Biochemical Pharmacology,* Vol. 34, pp. 1841–1843, 1985).

Similarly, the present inventors have shown that neocuproine, a chelator that effectively binds iron and copper and easily penetrates into cells, provides marked protection against ischemic-induced arrhythmias and against loss of cardiac function in the isolated rat heart using the Langendorff configuration (Y. J. Appelbaum, G. Uretzky, and M. Chevion, "The Protective Effect of Neocuproine on Cardiac Injury Induced by Oxygen Active Species in the Presence of Copper Sulfate", *Journal of Molecular and Cellular Cardiology,* Vol. 19 (Supp. III), Abstract No. 8, 1987; J. Kuvin, Y. J. Appelbaum, M. Chevion, J. B. Borman and G. Uretzky, "Role of Oxygen-Free Radicals in Reperfusion-Induced Arrhythmias: Protection by Neocuproine", *Journal of Molecular and Cellular Cardiology,* Vol. 19 (Supp. III), Abstract No. 150, 1987; Y. J. Appelbaum, J. Kuvin, J. B. Borman, G. Uretzky, and M. Chevion, "Role of Oxygen-Free Radicals in Reperfusion-Induced Arrhythmias: Protection by Neocuproine", *Free Radicals in Biology and Medicine,* Vol. 8, pp. 133–143, 1990).

The protective effect of another chelator, TPEN, has also been demonstrated by the inventors (Y. J. Appelbaum, J. Kuvin, M. Chevion and G. Uretzky, "TPEN, A Heavy Metal Chelator, Protects the Isolated Perfused Rat Heart from Reperfusion-Induced Arrhythmias", *Journal of Molecular and Cellular Cardiology,* Vol. 20 (Supp. V), Abstract No. 32, 1988; Y. J. Appelbaum, M. Bublil, J. B. Borman, G. Uretzky and M. Chevion, "Role of the Metal Chelator TPEN against Ischemic and Reperfusion Injury in the Isolated Perfused Rat Heart", *Proceedings of the SOD V Conference,* Jerusalem, Israel, p. 135, Sep. 17–22, 1989; M. Karck, Y. Appelbaum, H. Schwalb, A. Haverich, M. Chevion and G. Uretzky, "TPEN, A Transition Metal Chelator, Improves Myocardial Protection during Ischemia", *Journal of Heart and Lung Transplantation,* Vol. 11, pp. 979–985, 1992).

It has now been found by the applicant that the complex Ga-DFO possesses the characteristics which could markedly improve the pharmaceutical efficacy of Desferal®.

This will be achieved by markedly enhancing its permeability into cells, and by the consequent significant increase of its capacity to bind intracellular iron and copper. In these chelates, the transition metals are not redox-active and cannot mediate free radical production. Concomitantly with the binding of copper and iron, "free" Ga is released from its complex with DFO or penicillamine, in a controlled mode that is fully dependent on the level of cell saturation with "free" iron and cooper. As Ga is approved as a drug in diagnosis of cardiac function and focal inflammation in human patients, and as DFO is an approved drug (patent protection expired), the approval of this combination for clinical trials for treatment of ischemic injury, radiotherapy and chemotherapy, iron-overload in thallasemia, paraquat intoxication, and in other instances where free radicals are implicated, should smoothly be carried through. Additionally, the Ga-DFO complex is permeable, and thus can be administered orally, providing a prominent advantage over the current procedures for administering Desferal®. This is also true for the complex with penicillamine, which is usually given per os.

The present invention provides a method for treatment of a disease selected from the group consisting of free radical induced pathological conditions, ischemic insult to the heart, eye, brain or kidney, thallasemia, hemochromatosis, Wilson's disease and paraquat toxicity, comprising administrating to a subject in need of such treatment a therapeutically effective amount of a pharmaceutical composition comprising a gallium complex selected from the group consisting of desferrioxamine and penicillamine in combination with a pharmacologically acceptable carrier.

The present invention also provides a pharmaceutical composition comprising a Ga complex of penicillamine, alone or in combination with complexes of Zn and/or Mn as active ingredients therein, in combination with a pharmacologically acceptable carrier.

The invention further provides a gallium desferrioxamine or gallium penicillamine complex for medical use, for exchanging gallium for iron.

Also provided according to the present invention is a gallium penicillamine complex per se.

In U.S. Pat. No. 5,075,469 there is described and claimed a pharmaceutical composition, comprising, in a pharmaceutically acceptable carrier, a zinc complex of desferrioxamine. Said patent, however, does not teach or suggest the subject matter of the present invention and was not obvious for several reasons to the present inventor, who also was the inventor of said patent.

As is known, zinc is a trace element found in all living tissues, including the human body. There it serves many functions, including enzymatic activities. In contrast, gallium is a trace element to which no natural biological activity has been assigned and there is no known essential requirement for its presence in tissues.

Zinc has been known for 20 years as an anti-oxidant metal (M. Chvapil, "New Aspects in the Biological Role of Zinc: A Stabilizer of Macromolecules and Biological Membranes", *Life Sciences,* Vol. 13, pp. 1041–1049, 1973; P. Korbashi, J. Katzhendler, P. Saltman and M. Chevion, "Zinc Protects E. Coli against Copper-Mediated Paraquat-Induced Damage", *Journal of Biological Chemistry*, Vol. 264, pp. 8479–8482, 1989; S. Powell, P. Saltman, G. Uretzky and M. Chevion, "The Effect of Zinc on Reperfusion Arrhythmias in the Isolated Perfused Rat Heart", *Free Radicals in Biology and Medicine*, Vol. 8, pp. 33–46, 1990). In contrast, there are no reports for the anti-oxidative activities of gallium or gallium complexes.

Furthermore, while zinc is a bivalent cation (ZnII), gallium is a trivalent ion (GaIII).

As reported by H. Keberle, "Biochemistry of Desferrioxamine and Its Relation to Iron Metabolism", *Annals of the New York Academy of Sciences*, Vol. 119, pp. 758–762, 1964, the DFO molecule is made up of six basic units. In this form, when it is not bound to metals, it is a linear molecule that cannot easily penetrate into most cells (R. Laub, Y. J. Schneider, J. N. Octave, A. Trouet and R. R. Crichton, "Cellular Pharmacology of Desferrioxamine B and Derivatives in Cultured Rat Hepatocytes in Relation to Iron Mobilization", *Biochemical Pharmacology*, Vol. 34, pp. 1175–1183, 1985).

Based on the similarity of the ligand chemistry between iron or copper, on one hand, and gallium on the other, it is reasonable to assume that the structure of Ga-DFO is also spherical (rather than linear). In addition, metal binding to the negatively-charged DFO renders the molecule less polar. These considerations might explain why the complexes could more easily penetrate through cellular membranes and biological barriers, and more effectively bind intracellular metals that are redox-active and mediate tissue damage. In this process, two steps provide antioxidant protection: a) the removal of redox-active iron and copper by their chelation; and b) the controlled release of "free" Ga, which has now been found to compete for iron binding sites and to act as an anti-oxidant species.

Thus, based on thermodynamic and kinetic measurements, upon penetration into cells with high abundance of low molecular weight and redox-active complexes of iron or copper, it is assumed that the Ga-DFO complex exchanges the Ga with iron or copper instantaneously and protects the cell against damage.

The present preparations should contain the following components:

A. For treatment by injection:
 1. $GaCl_3$/Desferal® (molar ratios Ga/DFO between 0.1:1.0 and 1.0:1.0), in isotonic solution
B. For oral use: capsules, tablets, or drinkable preparation should contain:
 1. Ga/Desferal® (molar ratios between 0.6:1.0 and 1.0:1.0)
 2. $GaCl_3$/penicillamine (molar ratios Ga/penicillamine 0.1:1.0 and 1.0:1.0)
C. For treatment by injection:
 1. A combination of Ga/DFO (1:1) with Mn/DFO (i:1) with a ratio of Ga/Mn between 10 and 1.0
 2. A combination of Ga/DFO (1:1) with Zn/DFO (1:1) with a ratio of Ga/Zn between 10 and 0.1
 3. A combination of Ga/DFO (1:1), Zn/DFO (1:1) and Mn/DFO, with a ratio of Ga/Zn/Mn between 1:1:1 and 1:0.1:0.01
D. For treatment by injection:
 1. A combination of $^{67}Ga$ (radioactive) and DFO (molar ratio 1:1) for diagnosis of cardiac function and focal inflammation by imaging with gamma-ray camera
 2. A combination of Ga/DFO (1:1) for protection of the dystrophied heart and maintaining adequate myocardial function While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Ga-DFO Complex (GMC-1)

10 mM solution of Desferal® (Ciba-Geigy, Basle) is mixed with an equal volume of 10 mM of $GaCl_3$ (A.R.) solution, titrated to pH 5.0 with $NaHCO_3$ and then with NaOH (1M) to pH 7.4. Ga-DFO is formed. The ratio Ga/DFO is 1.0:1.0. The recommended concentration in blood is 3–50 μM.

EXAMPLE 2

Ga-DFO Complex (GMC-2)

5 mM solution of Desferal® (Ciba-Geigy, Basle) is mixed with an equal volume of 3 mM solution of $GaCl_3$ solution, titrated to pH 7.4. The complex Ga-DFO is formed. The ratio Ga/DFO is 0.6:1.0.

EXAMPLE 3

Ga-DFO Complex in Combination with Zn-DFO Complex 10 mM solution of GMC-1 mixed with an equal volume of 10 mM solution of Zn-DFO (1:1) as prepared according to U.S. Pat. No. 5,075,469. The ratio Ga/Zn/DFO is 1:1:2.

EXAMPLE 4

Ga-DFO Complex in Combination with Zn-DFO Complex 10 mM solution of GMC-1 is mixed with an equal volume of 2 mM solution of Zn-DFO (1:1) prepared according to U.S. Pat. No. 5,075,469. The ratio Ga/Zn/DFO is 1:0.2:1.2.

EXAMPLE 5

Combination of Ga-DFO, Zn-DFO and Mn-DFO Complexes 10 mM solution of GMC-1 is mixed with 1 ml of 10 mM solution of Zn/DFO (1:1) and 1 ml of 10 mM solution Mn/DFO (1:1). The ratio Ga/Zn/Mn/DFO is 1.0:1.0:1.2.

EXAMPLE 6

Ga-Penicillamine Complex

D-penicillamine (Aldrich Chemical Co., Inc.) 30 mM in doubly distilled water is mixed with equal volume of 30 mM $GaCl_3$. The complex Ga-penicillamine (1.0:1.0) is formed.

EXAMPLE 7

A Combination of Ga-Penicillamine and Zn-Penicillamine Complexes 10 mM solution of Ga-penicillamine complex is mixed with 0.1 volume of 10 mM Zn-Penicillamine complex. The ratio Ga/Zn/Penicillamine is 1:0.1:1.1.

EXAMPLE 8

Pharmaceutical Preparation of Ga-Desferal® Complex for I.V. Injection 10 mM solution of GMC-1 in saline is prepared and sterilized by ultra filtration or by autoclaving. A typical dose would be 0.02–0.2 ml/kg of body weight.

EXAMPLE 9

Pharmaceutical Preparation of Ga-DFO Complex for Oral Administration 10 ml of sterile solution containing 500 mg Desferal®, 133.4 mg of $GaCl_3$ and 1 gr of glucose is prepared by dissolving the contents of one vial of Desferal® in $GaCl_3$/glucose sterile solution.

EXAMPLE 10

Pharmaceutical Preparation of Ga-Penicillamine Complex for Oral Administration A solution containing 250 mg of D-penicillamine is dissolved in doubly distilled water, and a solution containing 293.6 mg $GaCl_3$ in doubly distilled water is added together with 1 gr of glucose, and then lyophilize-dried. The solid is finely pulverized and inserted into commercial gelatin capsules.

EXAMPLE 11

Pharmaceutical Preparation of Ga-Penicillamine Complex for Oral Administration 250 mg of D-penicillamine, 293.6 mg $GaCl_3$ and 1 gr of glucose are dissolved in doubly distilled water and lyophilize-dried. The solid is collected, finely pulverized and compressed into tablets, using commercial binders and disintegrators.

EXAMPLE 12

GMC-1 Protects against Cardiac Damage to the Isolated Rat Heart in the Langendorff Configuration: LAD Occlusion The experiments and analysis were conducted in an analogous mode as described in S. Powell, P. Saltman, G. Uretzky and M. Chevion, "The Effect of Zinc on Reperfusion Arrhythmias in the Isolated Perfused Rat Heart", *Free Radicals in Biology & Medicine*, Vol. 8, pp. 33–46, 1990. Following 10 min. of steady state (stabilization), the LAD is occluded for 10 min. and then reopened. The protection observed, in the reperfusion phase, with 5 µM (micromolar) GMC-1 is 80%, 88% and 87% for P (peak left ventricular pressure), +dP/dt and −dP/dt, respectively. Additionally, 5 µM GMC-1 provided nearly complete (>95%) protection against reperfusion-induced arrhythmias.

EXAMPLE 13

GMC-1 Protects against Cardiac Damage to the Isolated Rat Heart in the Langendorff Configuration: Global Ischemia The experiments and analysis were conducted in an analogous mode as described in M. Chevion, Y. Jiang, R. Har-El, E. Berenshtein, G. Uretzky and N. Kitrossky, "Copper and Iron Are Mobilized Following Myocardial Ischemia: Possible Predictive Criteria for Tissue Injury", *Proceedings of the National Academy of Sciences*, U.S.A., Vol. 90, pp. 1102–1106, 1993. Following 10 min of steady state (stabilization), the heart is subjected to global ischemia by cutting off the supply of perfusate for 18 and 35 min., and then perfusion resumed. The protection observed in the reperfusion phase, with 5 µM (micromolar) GMC-1 is 97%, 109% and 107% for 18 min. and 73%, 39% and 40% for 35 min. ischemia for P, +dP/dt and −dP/dt, respectively.

EXAMPLE 14

Displacement of Ga within Ga-DFO Complex by Iron

Ga-DFO complex (1:1, 0.2 mM) was prepared and its spectrum taken. Small volume aliquots of ferric chloride ($FeCl_3$, 100 mM) were added to reach a final concentration of Fe(III) 0.05–0.20 mM. Spectrophotometric examination shows the immediate formation of a stoichiometric complex of ferric-DFO, which has a characteristic absorbance of 425 nm.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for treatment of a disease selected from the group consisting of free radical induced pathological conditions, ischemic insult to the heart, eye, brain or kidney, tahallasemia, hemochromatosis, Wilson's disease and paraquat toxicity, comprising administering to a subject in need of such treatment a therapeutically effective amount of a pharmaceutical composition comprising a gallium desferrioxamine complex or a gallium penicillamine complex in combination with a pharmacologically acceptable carrier.

2. A method for treatment of a disease according to claim 1, wherein the gallium complex is a gallium penicillamine complex.

3. A method for treatment of a disease according to claim 1, wherein said pharmaceutical composition comprises a gallium desferrioxamine complex in combination with a complex selected from the group consisting of zinc-desferrioxamine, manganese-desferrioxamine and combinations thereof as the active ingredient in combination with a pharmacologically acceptable carrier.

4. A pharmaceutical composition comprising a gallium complex of penicillamine as the active ingredient in combination with a pharmacologically acceptable carrier.

5. A pharmaceutical composition comprising a gallium complex of penicillamine as the active ingredient in combination with a pharmacologically acceptable carrier in a therapeutically effective amount for treatment of a disease selected from the group consisting of free radical induced pathological conditions, ischemic insult to the heart, eye, brain or kidney, thallasemia, hemochromatosis, Wilson's disease and paraquat toxicity.

6. A pharmaceutical composition comprising a gallium complex of penicillamine as the active ingredient in combination with a pharmacologically acceptable carrier in a therapeutically effective amount for treatment of free radical-induced pathological conditions.

7. A pharmaceutical composition comprising a gallium complex of penicillamine as the active ingredient in combination with a pharmacologically acceptable carrier in a therapeutically effective amount for treatment of injury resulting from ischemic insult to the heart, eye, brain or kidney.

8. A pharmaceutical composition comprising a gallium complex of penicillamine as the active ingredient in combination with a pharmacologically acceptable carrier in a therapeutically effective amount for treatment of thallasemia.

9. A pharmaceutical composition comprising a gallium complex of penicillamine acceptable the active ingredient in combination with a pharmacologically acceptable carrier in a therapeutically effective amount for treatment of hemochromatosis.

10. A pharmaceutical composition comprising a gallium complex of penicillamine as the active ingredient in combination with a pharmacologically acceptable carrier in a therapeutically effective amount for treatment of Wilson's disease.

11. A pharmaceutical composition comprising a gallium complex of penicillamine as the active ingredient in combination with a pharmacologically acceptable carrier in a therapeutically effective amount for treatment of paraquat toxicity.

12. A gallium penicillamine complex.

* * * * *